United States Patent [19]

Minami et al.

[11] 4,017,622
[45] Apr. 12, 1977

[54] PIPERAZINE DERIVATIVES

[75] Inventors: Shinsaku Minami, Yamatokouriyama; Jun-Ichi Matsumoto, Takatsuki; Minoru Sugita, Kyoto; Masanao Shimizu, Kobe; Yoshiyuki Takase, Amagasaki; Shinichi Nakamura, Takatsuki, all of Japan

[73] Assignee: Dainippon Pharmaceutical Co., Ltd., Osaka, Japan

[22] Filed: Jan. 30, 1975

[21] Appl. No.: 545,549

Related U.S. Application Data

[63] Continuation-in-part of Ser. No. 424,697, Dec. 14, 1973, abandoned.

[30] Foreign Application Priority Data

| Dec. 18, 1972 | Japan | 47-126968 |
|---|---|---|
| Dec. 18, 1972 | Japan | 47-126969 |
| Dec. 21, 1972 | Japan | 47-128441 |
| Apr. 17, 1973 | Japan | 48-43388 |
| Oct. 26, 1973 | Japan | 48-121057 |
| Oct. 26, 1973 | Japan | 48-121058 |
| Oct. 27, 1973 | Japan | 48-121006 |
| Nov. 6, 1973 | Japan | 48-124633 |

[52] U.S. Cl. .................. 424/250; 260/268 BC
[51] Int. Cl.² .............................. C07D 295/10
[58] Field of Search ........... 260/268 BC, 268 BQ; 424/250

[56] References Cited

UNITED STATES PATENTS 3,149,104  9/1964  Lesher .................. 260/268 BC

FOREIGN PATENTS OR APPLICATIONS 1,129,358  10/1968  United Kingdom

*Primary Examiner*—Paul M. Coughlan, Jr.
*Attorney, Agent, or Firm*—Sherman & Shalloway

[57] ABSTRACT

Piperazine derivatives of the following formula

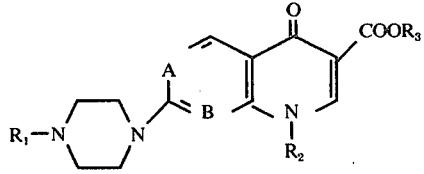

wherein A and B are a carbon atom or a nitrogen atom except the case where both A and B are nitrogen atoms, $R_1$ is hydrogen atom, an alkyl group having 1 to 4 carbon atoms, a benzyl group or acetyl group;

$R_2$ is a hydrogen atom, an alkyl group having 1 to 4 carbon atoms, a benzyl group or a vinyl group; and $R_3$ is hydrogen atom or an alkyl group having 1 to 6 carbon atoms, and pharmaceutically acceptable salts thereof.

16 Claims, No Drawings

PIPERAZINE DERIVATIVES

This application is a continuation-in-part application of copending application Ser. No. 424,697, filed Dec. 14, 1973, now abandoned.

This invention relates to new and useful piperazine derivatives having antibacterial activities, and also to their use.

This invention provides compounds of the following formula

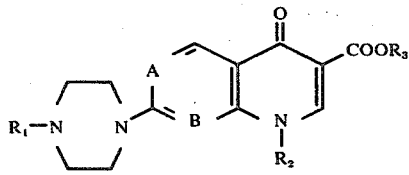

(I)

wherein
A and B are a carbon atom or a nitrogen atom except the case where both of A and B are nitrogen atoms,
$R_1$ is a hydrogen atom, an alkyl group having 1 to 4 carbon atoms, a benzyl group or acetyl group
$R_2$ is a hydrogen atom, an alkyl group having 1 to 4 carbon atoms, a benzyl group or a vinyl group
$R_3$ is a hydrogen atom or an alkyl group having 1 to 6 carbon atoms,
and salts thereof.

The following are preferred groups of compounds within formula [I] as antibacterial agents

| $R_1$ | $R_2$ | $R_3$ |
|---|---|---|
| hydrogen | ethyl | hydrogen |
| methyl | vinyl | |
| ethyl | | |

Especially suitable compounds are shown below.
1,4-Dihydro-1-ethyl-7-(4-methyl-1-piperazinyl)-4-oxoquinoline-3-carboxylic acid.
1,4-Dihydro-1-ethyl-7-(1-piperazinyl)-4-oxoquinoline-3-carboxylic acid.
1,4-Dihydro-1-ethyl-7-(4-methyl-1-piperazinyl)-4-oxo-1,6-naphthyridine-3-carboxylic acid.
1,4-Dihydro-1-ethyl-7-(1-piperazinyl)-4-oxo-1,6-naphthyridine-3-carboxylic acid.
1,4-Dihydro-1-ethyl-7-(1-piperazinyl)-4-oxo-1,8-naphthyridine-3-carboxylic acid.
1,4-Dihydro-7-(4-methyl-1-piperazinyl)-4-oxo-1-vinyl-1,8-naphthyridine-3-carboxylic acid.
1,4-Dihydro-7-(4-methyl-1-piperazinyl)-4-oxo-1-vinyl-1,6-naphthyridine-3-carboxylic acid.
1,4-Dihydro-7-(4-methyl-1-piperazinyl)-4-oxo-1-vinyl-quinoline-3-carboxylic acid.
1,4-Dihydro-7-(1-piperazinyl)-4-oxo-1-vinyl-1,8-naphthyridine-3-carboxylic acid.
1,4-Dihydro-7-(1-piperazinyl)-4-oxo-1-vinyl-1,6-naphthyridine-3-carboxylic acid.
1,4-Dihydro-7-(1-piperazinyl)-4-oxo-1-vinyl-quinoline-3carboxylic acid.
1,4-Dihydro-7-(4-ethyl-1-piperazinyl)-4-oxo-1vinyl-quinoline-3-carboxylic acid.
and pharmaceutically acceptable acid addition salts or alkali metal salts of these compounds.

The compounds of formula [I] are synthesized by any of the following process (a) to (d).

PROCESS (A) AMINATION

The compounds of formula [I] are obtained by reacting compounds (a) of the following formula

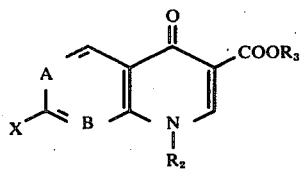

(a)

wherein
X is a halogen atom, and
$R_2$, $R_3$, A and B are the same as defined above with compounds (b) of the following formula

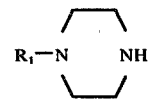

(b)

wherein $R_1$ is the same as defined above.

The reaction is performed by heating the compounds (a) and (b) together with a solvent, if desired, in a sealed reaction vessel. It is preferred to perform the reaction in the presence of a base, as a dehydrohalogenating agent, such as sodium bicarbonate, sodium carbonate, potassium carbonate, or triethylamine. Usually, the compounds (a) and (b) are used in stoichiometric amounts. Furthermore, the compounds (b) may be used in excess to make them serve also as a dehydrohalogenating agent. The compound (b) may be used in the form of a hydrate or acid addition salt of, for example, hydrochloric acid. The preferred reaction temperature is in the range of 60° C. to 200° C.

The solvent used in this reaction should be selected according to the properties of the starting materials to be used. Examples of the solvent are alcohols such as ethanol or propanol, aromatic hydrocarbons such as benzene or toluene, halogenoalkanes such as dichloroethane or chloroform, ethers such as tetrahydrofuran, dioxane or diphenyl ether, acetonitrile, dimethyl sulfoxide, dimethylformamide, and water. They may be used either alone or in mixture.

PROCESS (B) INTERMOLECULAR CYCLIZATION

Of the compounds of formula [I], those of the following formula

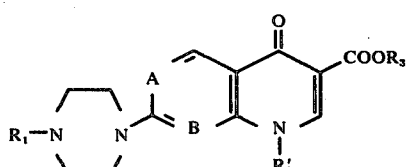

(I-A)

wherein $R'_2$ is a hydrogen atom, an alkyl group having 1 to 4 carbon atoms and $R_1$, $R_3$, A and B are the same as defined above, are obtained by heating compounds of formula (c)

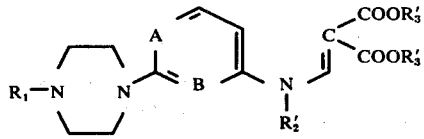

wherein R′₃ is an alkyl group having 1 to 6 carbon atoms and R₁, R′₂, A and B are the same as defined above, to induce intermolecular cyclization.

This reaction is performed by heating the compounds (c) directly or in a high-boiling solvent such as diphenyl ether, o-dichlorobenzene, diphenylene oxide, dibutyl phthalate, or mixtures of these. The suitable heating temperature is 140° to 260° C.

It is also possible to perform the cyclization reaction in the presence of a conventional cyclization agent such as polyphosphoric acid, a polyphosphoric acid alkyl ester, concentrated sulfuric acid or phosphorus pentoxide. Where polyphosphoric acid, a polyphosphoric acid alkyl ester or phosphorus pentoxide is used as the cyclization agent, the reaction is generally carried out in a solvent such as benzene, dioxane or dimethylformamide. When concentrated sulfuric acid is used, the reaction is generally carried out in a solvent such as acetic anhydride or acetic acid. Of course, depending upon the properties of the cyclization agent, it can be made to serve also as the solvent. If the cyclization agent is used, the reaction is carried out at relatively low temperature e.g. at a temperature of 100° to 160° C.

Where this reaction is carried out in the presence of a cyclization agent, the carboxylic acid ester portion sometimes undergoes hydrolysis and is converted to a free carboxylic acid.

PROCESS (C) ALKYLATION

Of the compounds of formula [I], those of the following formula

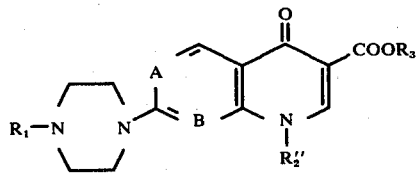

wherein
R″₂ is an alkyl group having 1 to 4 carbon atoms, a benzyl group, and
R₁, R₃, A and B are the same as defined above, are obtained by reacting compound (d)

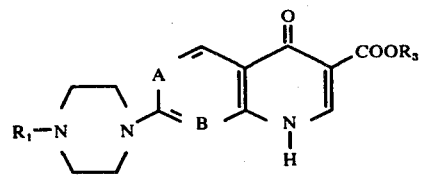

wherein R₁, R₃, A and B are the same as defined above, with an alkylating agent corresponding to R″₂.

Known alkylating agents can be used. Specific examples include alkyl halides such as methyl iodide, ethyl iodide, benzyl chloride, and lower alkyl esters such as dimethyl sulfate, diethyl sulfate, methyl p-toluenesulfonate, or triethyl phosphate.

This reaction is generally carried out by reacting the compound (d) with a stoichiometric amount of the alkylating agent in an inert solvent at an elevated temperature, e.g., of 25° to 150° C. If desired, the alkylating agent may be used in excess. The solvent may be either non-aqueous or hydrous. Examples of the solvent are ethanol, dioxane dimethylformamide, dimethyl sulfoxide and water. The reaction is promoted by adding an acid acceptor, for example, a base such an alkali carbonate, an alkali hydroxide, an alkali metal alkoxide, sodium hydride, triethylamine, benzyltrimethyl ammonium hydroxide. Where this reaction is carried out in a hydrous solvent, the carboxylic acid ester portion sometimes undergoes hydrolysis depending upon the reaction conditions, and is converted to a free carboxylic acid. Furthermore, when compounds of formula (d) in which R₁ is a hydrogen atom are alkylated, N-alkylated products at the 4-position of the piperazine nucleus can be obtained sometimes together with N-alkylated products at the 1-position of the quinoline or naphthyridine nucleus.

Accordingly, the desired products can be obtained by suitably choosing the starting material, solvent and alkylating agent.

PROCESS (D) HYDROLYSIS

Of the compounds of formula [I], those of the following formula

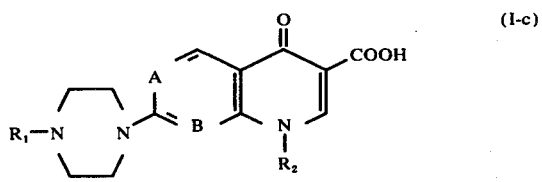

wherein
R₁, R₂, A and B are the same as defined above, are obtained by hydrolyzing compound (e)

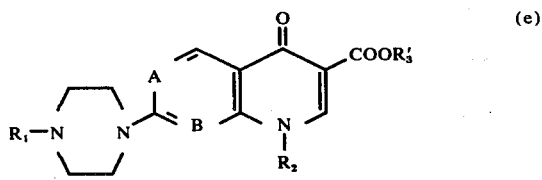

wherein
R₁, R₂ and R′₃ are the same as defined above.

This reaction is carried out by contacting the compound (e) with water. Generally, in order to promote the reaction, it is performed in the presence of a catalyst such as an acid or base.

Examples of the acid are inorganic acids such as hydrochloric acid, hydrobromic acid, hydroiodic acid, sulfuric acid or phosphoric acid, and organic acids such as acetic acid, oxalic acid or toluenesulfonic acid.

Examples of the base are alkali metal hydroxides such as sodium hydroxide or barium hydroxide, alkali metal carbonates such as sodium carbonate or potassium carbonate, and sodium acetate.

This reaction may also be performed by directly heating the material in the presence of the above acid, and then adding water. The solvent is usually water, but depending upon the properties of the material, a solvent such as ethanol, dioxane, ethyleneglycol dimethyl ether, benzene or acetic acid together with water may also be used. The reaction temperature may be room temperature, but usually 50° to 200° C., preferably 70° to 120° C.

When the compound in which $R_1$ is an acetyl group is hydrolyzed under the stronger reaction conditions, the acetyl group and $R'_3$ group are split off by hydrolysis.

Of the starting compounds (a), those in which $R_2$ is a hydrogen atom or an alkyl group having 1 to 4 carbon atoms are obtained in the same manner as in the process (b), and those in which $R_2$ is a benzyl group are obtained in the same manner as in the process (c). Of the starting compound (a) those in which $R_2$ is a vinyl group are obtained by reacting compounds (d) and a 1,2-dihalogenoethane (e.g. 1,2-dichloroethane, 1,2-dibromoethane) in the same manner as in the process (c) to form halogenoalkylated compounds and then heating the compounds at 50° to 270° C in the presence of a base (e.g., potassium carbonate, sodium hydroxide, or pyridine).

The starting compounds (c) are obtained in accordance with the method disclosed in British Patent Specification No. 1,129,358.

This reaction is shown schematically as follows.

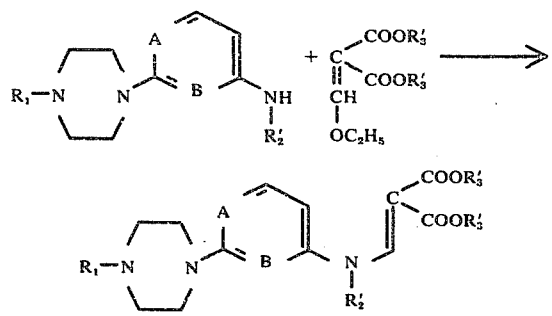

wherein $R_1$, $R'_2$, $R'_3$, A and B are the same as defined above.

The starting compound (d) and (e) are obtained in the same manner as in the process (a) or (b).

The compounds of the present invention prepared in the above process can be isolated and purified by the usual methods. The compounds [I] can be obtained in the free state or in the form of a salt depending upon the selection of the starting compounds and the reaction conditions. Furthermore, the compounds [I] can be converted to pharmaceutically acceptable amine salts or carboxylic acid salts by treatment with acid or alkali, or vice versa. The acid may be a variety of organic and inorganic acids, examples of which are hydrochloric acid, acetic acid, lactic acid, succinic acid, oxalic acid and methanesulfonic acid.

A clinical dosage of the compound [I] depends on the body weight, age and administration route but it is generally in the range of 100 mg – 5 g/day, preferably of 200 mg–3b/day.

The compounds [I] may be used as medicines, for example, in the form of pharmaceutical preparations containing the compound in admixture with an organic or inorganic, solid or liquid pharmaceutical adjuvant suitable for peroral, parenteral, enteral or local administration. Pharmaceutically acceptable adjuvants are substances that do not react with the compounds, and include, for example, water gelatin, lactose, starch, cellulose, preferably microcrystalline cellulose, carboxymethyl cellulose, methyl cellulose, sorbitol, magnesium stearate, talc, vegetable oils, benzyl alcohol, gums, propylene glycol, polyalkylene glycols, methylparaben and other known medicinal adjuvants. The pharmaceutical preparations may be, for example, powder, tablets, ointments, suppositories, creams or capsules, or in liquid form as solutions, suspensions or emulsions. They may be sterilized and/or contain assistants such as preserving, stabilizing, wetting or emulsifying agents, salts for regulating the osmotic pressure or buffers. They may further contain other therapeutically valuable substances. The preparations are formed by conventional methods.

The antibacterial activities of the typical compounds of this invention are shown in Tables I – III together some of the known compounds.

In the Tables II and III, the $ED_{50}$ and $LD_{50}$ values were calculated in accordance with the Bcherns-Kaerber method [Arch. Exp. Path, Pharm., 162, 480 (1931)].

The numbers of the tested compounds are those described in the Example.

The known compounds, PA, NA and AT-1249, are as follows:

PA: 5,8-Dihydro-8-ethyl-2-pyrrolidino-5-oxopyrido[2,3-d]pyrimidine-6-carboxylic acid which is the most valuable compound in British Patent No. 1,129,358.

NA: 7-Methyl-4-oxo-1,8-naphthylidine-3-carboxylic acid (Nalidixic acid) which is disclosed in U.S. Pat. No. 3,149,104.

AT-1249: 7-Dimethylamino-4-oxo-1-ethyl-1,8-naphthylidine-3-carboxylic acid which is disclosed in U.S. Pat. No. 3,149,104.

Table I

1) *In vitro* antibacterial activity against 3 strains of bacteria

| AT No | Compound | Staphylococcus aureus Terajima | Escherichia coli K-12 | Pseudomonas aeruginosa Tsuchijima |
|---|---|---|---|---|
| 1091 | (structure shown) | 30 | 1 | 10 |

Table I-continued

1) *In vitro* antibacterial activity against 3 strains of bacteria

| AT No | Compound | Staphylococcus aureus Terajima | Escherichia coli K-12 | Pseudomonas aeruginosa Tsuchijima |
|---|---|---|---|---|
| 1090 | (7-(4-methylpiperazin-1-yl)-1-ethyl-4-oxoquinoline-3-carboxylic acid*) | 30 | 1 | 30 |
| 1162 | (7-(piperazin-1-yl)-1-benzyl-4-oxoquinoline-3-carboxylic acid) | 30 | 1 | 10 |
| 1147 | (7-(4-methylpiperazin-1-yl)-1-benzyl-4-oxoquinoline-3-carboxylic acid) | >100 | 1 | 10 |
| 1214 | (7-(piperazin-1-yl)-1-ethyl-4-oxo-1,8-naphthyridine-3-carboxylic acid) | 30 | 3 | 10 |
| 1225 | (7-(4-methylpiperazin-1-yl)-1-ethyl-4-oxo-1,8-naphthyridine-3-carboxylic acid) | 100 | 1 | 30 |
| 1276 | (7-(4-methylpiperazin-1-yl)-1-vinyl-4-oxo-1,8-naphthyridine-3-carboxylic acid) | >100 | 1 | 10 |
| 1424 | (7-(piperazin-1-yl)-1-vinyl-4-oxo-1,8-naphthyridine-3-carboxylic acid*) | 100 | 1 | 10 |
| 1493 | (7-(4-methylpiperazin-1-yl)-1-vinyl-4-oxoquinoline-3-carboxylic acid) | 100 | 1 | 3 |

Table I-continued

1) In vitro antibacterial activity against 3 strains of bacteria

| AT No | Compound | Staphylococcus aureus Terajima | Escherichia coli K-12 | Pseudomonas aeruginosa Tsuchijima |
|---|---|---|---|---|
| 1557 | (7-(4-ethyl-piperazinyl)-1-vinyl-quinolone-3-carboxylic acid) | 30 | 1 | 10 |
| 1367 | (7-piperazinyl-1-ethyl-naphthyridine-3-carboxylic acid) | >100 | 3 | 30 |
| 1317 | (7-(4-methyl-piperazinyl)-1-ethyl-naphthyridine-3-carboxylic acid) | 30 | 3 | 100 |
| 1249 | (7-dimethylamino-1-ethyl-naphthyridine-3-carboxylic acid) | 100 | 1 | >100 |
| NA | (7-methyl-1-ethyl-naphthyridine-3-carboxylic acid) | 100 | 1 | 100 |
| PA | (pyrrolidinyl-amidino-1-ethyl-naphthyridine-3-carboxylic acid) | 10 | 1 | 100 |

*hydrochloride

The minimum inhibitory concentration (MIC) was determined by the well known serial dilution method.
    Experimental conditions:
    Medium:     nutrient broth, pH 7.0 (5 ml/tube)
    Inoculum:   1 drop of 1 : 10⁵ dilution of an overnight broth culture per tube
    Incubation temperature and time:
        37° C for 48 hours.

Table II

2) In vivo efficacy against systemic infection with Pseudomonas aeruginosa and Salmonella typhimurium in mice

| Compound (At-No) | Pseudomonas aeruginosa* $ED_{50}$ (mg/kg) ip | Salmonella typhimurium** $ED_{50}$ (mg/kg) ip | Salmonella typhimurium** $ED_{50}$ (mg/kg) po |
|---|---|---|---|
| 1090 | 91.4 | 9.6 | 13.6 |
| 1091 | 6.3 | 15.5 | ≈109 |
| 1214 | 9.2 | 18.7 | ≈43.8 |
| 1367 | ≈12.5 | 54.5 | 70.7 |
| 1317 | 50.0 | 14.9 | 23.9 |

Table II-continued

2) *In vivo* efficacy against systemic infection with Pseudomonas aeruginosa and Salmonella typhimurium in mice

| Compound (AT-No) | Pseudomonas aeruginosa* $ED_{50}$ (mg/kg) ip | Salmonella typhimurium** $ED_{50}$ (mg/kg) ip | Salmonella typhimurium** $ED_{50}$ (mg/kg) po |
|---|---|---|---|
| 1424 | 3.9 | 19.3 | 22.9 |
| 1493 | 17.8 | 3.4 | 8.8 |
| 1557 | 19.3 | 5.1 | 11.5 |
| 1249 | >100 | — | — |
| NA | >100 | 18.9 | 18.9 |
| PA | >100 | 43.5 | 46.7 |

*Experimental conditions:
 Organism: Pseudomonas aeruginosa No. 12
 Mice: male mice (ddY-S) weighing 20 g approximately.
 Infection: intraperitoneal infection with 50 to 100 $LD_{50}$ (about $5 \times 10^3$ cells/mouse) of a bacterial suspension in 4% gastric mucin.
 Medication: twice, about 5 minutes and 6 hours after infection.
 Drug: an alkaline solution (pH 8 – 9) for intraperitoneal administration.
 Observation: 7 days.
 ip: intraperitoneal administration.
**Experimental conditions:
 Organism: Salmonella typhimurium S-9
 Ice: male mice (ddY-S) weighing 20 g approximately.
 Infection: Intraperitoneal infection with 50 to 100 $LD_{50}$ (about $10^5$ cells/mouse) of a bacterial suspension in a nutrient broth.
 Medication: twice a day for 4 days from the day of infection.
 Drug: an alkaline solution (pH 8 – 9) for intraperitoneal administration and suspension in 0.2% carboxymethyl cellulose for oral administration.
 Observation: 14 days.
 ip: intraperitoneal administration.
 po: oral administration.
3) Acute toxicity in mice

Table III

| Compound (AT No) | $LD_{50}$ (mg/kg) iv | $LD_{50}$ (mg/kg) po |
|---|---|---|
| 1090 | >500 | 2000 |
| 1091 | >500 | 2000 |
| 1214 | >500 | — |
| 1317 | >500 | — |
| 1424 | 354 | >2000 |
| 1493 | >500 | >2000 |
| 1557 | 354 | >2000 |
| NA | 268 | 1516 |
| PA | 267.9 | >4000 |

Experimental conditions:
 Mice: male mice (ddY-S) weighing 20 g approximately
 Drug: alkaline solution (pH 8 – 9) for intravenous administration and suspension in 0.2% carboxymethyl cellulose for oral administration.
 Observation: 7 days.
 iv: intravenous administration.
 ip: oral administration.

EXAMPLE 1

1,4-Dihydro-1-ethyl-4-oxo-7-(1-piperazinyl) quinoline-3-carboxylic acid (AT-1195) and its hydrochloride (AT-1091)

A mixture containing 1.5 g of 7-chloro-1,4-dihydro-1-ethyl-4-oxoquinoline-3-carboxylic acid, 5.0 g of piperazine hexahydrate and 8 ml of water was heated in a sealed tube at 170° C for 18 hours. The reaction mixture was shaken with chloroform to remove the material soluble in the organic solvent. The resulting aqueous layer was treated with decolorizing charcoal and acidified with hydrochloric acid to give a precipitate, which was collected and recrystallized from a mixture of ethanol and water to yield 1.35 g of the hydrochloride, m.p. above 300° C.

The hydrochloride was dissolved in hot water and the solution was adjusted to pH 7.5 – 8.0 with a 10% aqueous solution of sodium hydroxide. The resulting free carboxylic acid was collected and recrystallized from a mixture of dimethylformamide and water, m.p. 272° – 275° C.

EXAMPLE 2

1,4-Dihydro-1-ethyl-7-(4-methyl-1-piperazinyl)-4-oxo-quinoline-3-carboxylic acid. (AT-1174)

A mixture containing 0.95 g of 7-chloro-1-ethyl-1,4-dihydro-4-oxoquinoline-3-carboxylic acid, 0.85 g of 1-methyl piperazine and 6 ml of water was heated in a sealed tube at 170° C which was collected and recrystallized from a mixture of ethanol and water to yield 1.35 g of the hydrochloride, m.p. about 300° C. for 15 hours. The reaction mixture was shaken with chloroform to remove the material soluble in the organic solvent. The resulting aqueous layer was neutralized with acetic acid to give a solid which was collected, washed with water, and recrystallized from a mixture of dimethylformamide and water to yield 0.81 g of the product, m.p. 220.5° – 225.5° C.

EXAMPLE 3

1,4-Dihydro-1-ethyl-7-(4-methyl-1-piperazinyl)-4-oxo-1,6-naphthyridine-3-carboxylic acid. (AT-1317)

To a suspension of 1.27 g of 7-chloro-1,4-dihydro-1-ethyl-4-oxo-1,6-naphthyridine-3-carboxylic acid in 35 ml of ethanol was added 1.25 g of 1-methylpiperazine, and the mixture was heated to reflux for 15 hours. The

EXAMPLE 4

Ethyl 1,4-dihydro-1-ethyl-4-oxo-7-(1-piperazinyl)-1,6-naphthyridine-3-carboxylate. (AT-1388)

A mixture containing 1.40 g of ethyl 7-chloro-1,4-dihydro-1-ethyl-4-oxo-1,6-naphthyridine-3-carboxylate, 2.0 g of piperazine hexahydrate and 50 ml of ethanol was heated to reflux for 12 hours. The reaction mixture was concentrated and chilled to give a solid, which was collected and recrystallized from ethyl acetate to yield 1.53 g of the product as yellow powder, m.p. 169° – 170° C.

EXAMPLE 5

1,4-Dihydro-1-ethyl-4-oxo-7-(1-piperazinyl)-1,8-naphthyridine-3-carboxylic acid. (AT-1214)

To a suspension of 2.53 g of 7-chloro-1-ethyl-1,4-dihydro-4-oxo-1,8-naphthyridine-3-carboxylic acid in 90 ml of acetonitrile was added 5.82 g of piperazine hexahydrate. The mixture was allowed to stand with stirring at room temperature for 3 hours and then concentrated to dryness in vacuo. The resulting residual solid was taken in 15 ml of a 10% aqueous solution of potassium hydroxide. The solution was adjusted to pH 8 – 9 by addition of acetic acid to yield a solid, on cooling, which was collected, washed with water, and recrystallized from water to give 2.3 g of the product as colorless needles, m.p. 271° – 272° C.

EXAMPLE 6

1,4-Dihydro-4-oxo-7-(1-piperazinyl)-1-vinyl-quinoline-3-carboxylic acid hydrochloride. (AT-1412)

A mixture containing 1.0 g of 7-chloro-1,4-dihydro-4-oxo-1-vinylquinoline-3-carboxylic acid, 6.2 g of piperazine hexahydrate and 30 ml of dimethylformamide was heated at 110° C for 4 hours with stirring. The reaction mixture was concentrated to dryness in vacuo and to the resulting residue was added successively 50 ml of water and 5 ml of acetic acid. The acidic mixture was heated on a steam bath for 3 – 5 minutes and filtered to remove the insoluble material. After concentration of the filtrate to dryness, the resulting residue was taken in 40 ml of water. To the aqueous solution was added about 5 ml of 20% hydrochloric acid and then the solution was chilled to separate out a solid. The collected solid was recrystallized from a mixture of methanol and water containing a drop of 20% hydrochloric acid to give 0.55 g of the product, m.p. 283° – 287° C with decomposition.

EXAMPLE 7

Ethyl 1,4-dihydro-7-(4-methyl-1-piperazinyl)-4-oxo-1,8-naphthyridine-3-carboxylate. (AT-1227)

A suspension of 1.6 g of diethyl 6-(4-methyl-1-piperazinyl)-2-pyridylaminomethylenemalonate in 12 ml of diphenyl ether was heated at 250° – 225° C for 15 minutes and then allowed to cool to room temperature. To the reaction mixture was added 12 ml of n-hexane. The resulting precipitate was collected, and recrystallized from ethanol to give 1.21 g of the product as yellow fine needles, m.p. 248.5° – 250° C with decomposition.

EXAMPLE 8

Ethyl 1,4-dihydro-1-ethyl-7-(4-methyl-1-piperazinyl)-4-oxo-1,8-naphthyridine-3-carboxylate A mixture containing 1.0 g of diethyl N-ethyl-N-[2-(4-methyl-1-piperazinyl)-6-pyridyl]aminomethylenemalonate and 6.0 g of polyphosphoric acid was heated at 140° C for 15 minutes, and then poured into ice-water. The resulting mixture was made alkaline with 28% aqueous ammonia and extracted with chloroform. The extract was washed with water and dried over anhydrous sulfate. Then the solvent was removed by distillation to leave a crude product which was recrystallized from n-hexane to yield 0.69 g of the product as pale yellow needles, m.p. 130° – 130.5° C.

EXAMPLE 9

7-(4-acetyl-1-piperazinyl)-1,4-dihydro-1-ethyl-4-oxo-1,8-naphthyridine-3-carboxylic acid. (AT-1250)

A mixture containing 1.58 g of 7-(4-acetyl-1-piperazinyl)-1,4-dihydro-4-oxo-1,8-naphthyridine-3-carboxylic acid, 10 ml of a 12% aqueous solution of sodium hydroxide, 5 ml of ethyl iodide, and 130 ml of dimethylformamide was heated at 90° C for 2 hours. The reaction mixture was concentrated to dryness in vacuo and the resulting residue dissolved in ca. 10 ml of water. The aqueous solution was neutralized with acetic acid to separate out a solid which was taken up in chloroform. The chloroform solution was filtered to remove the insoluble material and the solent distilled off to leave a solid which was recrystallized from ethanol to give 1.53 g of the product as colorless fine needles, m.p. above 300° C.

EXAMPLE 10

1,4-Dihydro-1-ethyl-4-oxo-7-(1-piperazinyl)quinoline-3-carboxylic acid (AT-1195)

To 2.0 g of ethyl 1,4-dihydro-1-ethyl-4-oxo-7-(1-piperazinyl)quinoline-3-carboxylate was added 10 ml of a 5% aqueous solution of potassium hydroxide. The mixture was heated at 90° C for 30 minutes with stirring and neutralized, under cooling, with acetic acid to separate out a solid which was collected, and recrystallized from a mixture of ethanol and water to give 1.85 g of the product, m.p. 272° – 275° C.

EXAMPLE 11

1,4-Dihydro-1-ethyl-4-oxo-7-(1-piperazinyl)-1,8-naphthyridine-3-carboxylic acid (AT-1214)

To 1.6 g of ethyl 7-(4-acetyl-1-piperazinyl)-1,4-dihydro-1-ethyl-4-oxo-1,8-naphthyridine-3-carboxylate was added 15 ml of a 10% aqueous solution of sodium hydroxide. The mixture was heated at 95° C for 1.5 hours, and neutralized, under cooling, with acetic acid to give a precipitate which was collected and recrystallized from water to yield 1.0 g of the product as colorless needles, m.p. 272° – 273° C.

EXAMPLE 12

1,4-Dihydro-1-ethyl-7-(4-methyl-1-piperazinyl)-4-oxo-quinoline-3-carboxylic acid hydrochloride (AT-1090)

To a mixture containing 2.0 g of ethyl 1,4-dihydro-7-(4-methyl-1-piperazinyl)-4-oxoquinoline-3-carboxylate, 20 ml of dimethylformamide, and 0.50 g of 65% sodium hydride was added 5 ml of ethyl iodide. The resulting mixture was heated at 90° C for 2 hours and then concentrated to dryness in vacuo. To the resulting residue was added 10 ml of a 5% aqueous solution of potassium hydroxide. The alkaline mixture was heated at 90° C for 30 minutes and after being cooled, shaken with chloroform to remove the material soluble in the organic solvent. The aqueous solution was adjusted to pH 2 – 3 with hydrochloric acid to yeild a precipitate which was collected and recrystallized from a mixture of ethanol and water to give 1.76 g of the product, m.p. above 300° C.

EXAMPLE 13

1,4-Dihydro-4-oxo-7-(4-methyl-1-piperazinyl)-1-vinyl-1,8-naphthyridine-3-carboxylic acid (AT-1276)

To 0.80 g of ethyl 1-(2-chloroethyl)-1,4-dihydro-7-(4-methyl-1-piperazinyl)-4-oxo-1,8-naphthyridine-3-carboxylate was added 10 ml of a 10% aqueous solution of sodium hydroxide. The mixture was heated at 90° – 95° C for 30 minutes and neutralized with acetic acid under cooling. The resulting mixture was extracted with chloroform. The extract was washed with water and concentrated to leave a yellow solid which was collected and recrystallized from ethanol to give 0.56 g of the product as pale yellow needles, m.p. 238° – 239° C.

EXAMPLE 14

1,4-Dihydro-4-oxo-7-(1-piperazinyl)-1-vinyl-1,8-naphthyridine-3-carboxylic acid hydrochloride. (AT-1424)

To a solution of 2.5 g of 7-chloro-1,4-dihydro-4-oxo-1-vinyl-1,8-naphthyridine-3-carboxylic acid in 80 ml of ethanol was added 5.8 g of piperazine hexahydrate. The mixture was heated to reflux for 2 hours and concentrated to dryness under reduced pressure. To the resulting residue was added 10 ml of 1N-HCl. The crystal that separated on cooling was collected and dissolved in 40 ml of hot water. The solution with 0.5 g of charcoal was warmed for several minutes and filtered. The filtrate, after addition of 6 ml of 1H-HCl, was cooled to give 2.7 g of the product as colorless needles, m.p. 285° – 287° C (decomp.).

EXAMPLE 15

1,4-Dihydro-7-(4-methyl-1-piperazinyl)-4-oxo-1-vinyl-quinoline-3-carboxylic acid (AT-1493) and its hydrochloride (At-1492)

A mixture containing 5.0 g of 7-chloro-1,4-dihydro-4-oxo-1-vinylquinoline-3-carboxylic acid, 75 ml of dimethyl sulfoxide and 15 ml of 1-methylpiperazine was heated to 110° C for 3 hours with stirring and then concentrated to dryness under reduced pressure. The residue was triturated with methanol to give crystals, which were collected and recrystallized from dimethylformamide–water (1:1) to afford 2.85 g of the hydrochloride, m.p. > 300° C.

The hydrochloride (1.5 g) was dissolved in 200 ml of hot water and neutralized with 1N-NaOH solution. The crystals that separated on cooling were collected and recrystallized from acetonitrile to give 1.2 g of the AT-1493 as slightly hygroscopic pale yellow needles, m.p. 224° – 225° C.

EXAMPLE 16

The following compounds were prepared by the same way as in EXAMPLE 14

7-(4-Benzyl-1-piperazinyl)-1,4-dihydro-4-oxo-1-vinyl-1,8-naphthyridine-3-carboxylic acid (m.p. 203° – 205° C) (At-1430)

7-(4-Ethoxycarbonyl-1-piperazinyl)-1,4-dihydro-4-oxo-1-vinyl-1,6-naphthyridine-3-carboxylic acid (m.p. 206° – 208° C) (AT-1538)

1,4-Dihydro-7-(4-methyl-1-piperazinyl)-4-oxo-1-vinyl-1,6-naphthyridine-3-carboxylic acid (m.p. 229° – 230° C) (At-1541)

EXAMPLE 17

The following compounds were prepared by the same way as in EXAMPLE 15.

7-(4-Ethyl-1-piperazinyl)-1,4-dihydro-4-oxo-1-vinyl-quinolin-3-carboxylic acid, m.p. 211° – 213° C (At-1557).

7-(4-Benzyl-1-piperazynyl)-1,4-dihydro-4-oxo-1-vinyl-quinolin-3-carboxylic acid, m.p. 202° – 205° C (At-1532).

EXAMPLE 18

1,4-Dihydro-4-oxo-7-(1-piperazinyl)-1-vinyl-1,8-naphthyridine-3-carboxylic acid (AT-1475) and its methanesulfonate (AT-1495).

A suspension of 2.0 g of ethyl 1,4-dihydro-4-oxo-7-(1-piperazinyl)-1-vinyl-1,8-naphthyridine-3-carboxylate in 20 ml of 5% NaOH solution was heated to 85° C for 15 minutes. The clear solution was acidified with acetic acid and then neutralized with 7% $NaHCO_3$ solution. The crystals that separated on cooling were collected by filtration and recrystallized from ethanol to give 1.68 g of the product (AT-1475) as pale yellow needles, m.p. 261°–263° C (decomp.).

To a suspension of 1.0 g of AT-1475 in 15 ml of water were added 0.5 ml of methanesulfonic acid and then 100 ml of ethanol. The yellow solution was cooled to 0° to give a precipitate, which was collected and washed with ethanol. The precipitate was dissolved in 10 ml of water and filtered to remove insoluble materials. To the filtrate was added ethanol to form 1.1 g of the methanesulfonate as yellow needles, m.p. 299°–301° C (decomp.).

EXAMPLE 19

Following the procedure described in Example 1, there is obtained 1,4-dihydro-1-ethyl-7-(4-methyl-1piperazinyl)-4-oxoquinoline-3-carboxylic acid hydrochloride, m.p. above 300° C. (AT-1090)

EXAMPLE 20

The following compounds wereprepared by the same was as in Example 2.

| | R₁ | R₂ | m.p. (° C) |
|---|---|---|---|
| AT-1124 | ⌬-CH₂- | C₂H₅- | 213.5 – 214.5 |
| AT-1147 | CH₃- | ⌬-CH₂- | 277 – 279 |
| AT-1162 | H | ⌬-CH₂- | 288 – 289 |

(Structure: 7-(4-R₁-piperazinyl)-1-R₂-1,4-dihydro-4-oxoquinoline-3-carboxylic acid)

EXAMPLE 21

Following the procedure described in Example 3, there is obtained 1,4-dihydro-1-ethyl-4-oxo-7-(1-piperazinyl)-1,6-naphthryridine-3-carboxylic acid, m.p. 294° – 296° C with decomposition. (AT-1367)

EXAMPLE 22

Following the procedure described in Example 4, there are obtained ethyl 1,4-dihydro-1-ethyl-7-(4-methyl-1-piperazinyl)-4-oxo-1,6-naphthyridine-3carboxylate, m.p. 176° – 177° C (AT-1387) and ethyl 7-(4-benzyl-1-piperazinyl)-1,4-dihydro-1-ethyl-4-oxo-1,6-naphthyridine-3-carboxylate, m.p. 172° –173° C. AT-1410)

EXAMPLE 23

The following compounds were prepared by the same way as in Example 5. (AT-1239): 7-(4-Benzyl-1-piperazinyl)-1,4-dihydro-1-ethyl-4- oxo-1,8-naphthyridine-3-carboxylic acid, m.p. 205.5° – 206.5° C. (At-1225): 1,4-Dihydro-1-ethyl-7-(4-methyl-1-piperazinyl)-4-oxo-1,8-naphthyridine-3-carboxylic acid, m.p. 233° – 235° C.
Ethyl 1,4-dihydro-1-ethyl-7-(4-methyl-1-piperazinyl)- 4-oxo-1,8-naphthyridine-3-carboxylate, m.p. 130° –130.5° C.

EXAMPLE 24

Following the procedure described in Example 6, there is obtained 1,4-dihydro-7-(1-piperazinyl)-4-oxo-1-vinyl-1,6-naphthyridine-3-carboxylic acid hydrochloride.

EXAMPLE 25

Following the procedure described in Example 7, there is obtained ethyl 1,4-dihydro-1-ethyl-7-(4methyl-1-piperazinyl)-4-oxo-1,6-naphthyridine-3-carboxylate, m.p. 176° – 177° C. (AT-1387)

EXAMPLE 26

The following compounds were prepared by the same method as in Example 9.
(AT-1410): Ethyl 7-(4-benzyl-1-piperazinyl)-1ethyl-1,4-dihydro- 4-oxo-1,6-naphthyridine-3-carboxylate, m.p. 172° – 173° C.
(AT-1225): 1,4-Dihydro-1-ethyl-7-(4-methyl-1-piperazinyl)-4-oxo 1,8-naphthyridine-3-carboxylic acid, m.p. 233° – 235° C.

EXAMPLE 27

The following compounds were prepared by the same way as in Example 10.

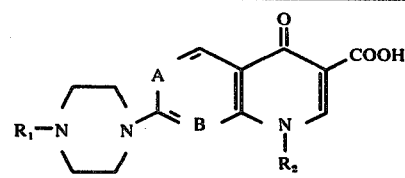

| AT | A | B | R₁ | R₂ | m.p. (° C) |
|---|---|---|---|---|---|
| 1174 | CH | CH | CH₃ | C₂H₅ | 220.5 – 222.5 |
| 1367 | N | CH | H | C₂H₅ | 294 – 296 (decomp.) |

-continued

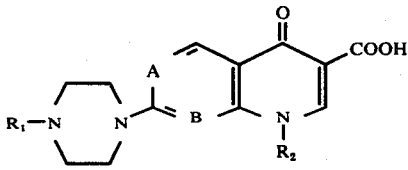

| AT | A | B | R₁ | R₂ | m.p. (° C) |
|---|---|---|---|---|---|
| 1406 | CH | N | H | benzyl (C₆H₅-CH₂) | 241 – 243 (decomp.) |
| 1225 | CH | N | CH₃ | C₂H₅ | 233 – 235 |
| 1239 | CH | N | benzyl (C₆H₅-CH₂) | C₂H₅ | 205.5 – 206.5 |

EXAMPLE 28

Following the procedure described in Example 13, there is obtained 1,4-dihydro-7-(1-piperazinyl)-4-oxo-1-vinyl-1,8-naphthyridine-3-carboxylic acid hydrochloride. m.p. 285° – 287° C with decomposition. (AT-1424)

The preparation for the intermediate compound of the formula (a) is illustrated in following Examples 29 to 32.

EXAMPLE 29

Ethyl 7-chloro-1,4-dihydro-4-oxo-1,6-naphthyridine3-carboxylate

A mixture containing 3.0 g of 4-amino-2-chloropyridine and 5.6 g of diethyl ethoxymethylenemolanate was heated at 95° C for 2 hours during which period ethanol that was formed in the course of the reaction was removed by distildation under reduced pressure. n-Hexane was added to the mixture. The resulting solid was collected, and recrystallized from n-hexane to give diethyl 2-chloro-4-pyridylamino-methylenemalonate, m.p. 60° – 62° C.

To 30 ml of boiling diphenyl ether was added the diester and the resulting mixture was held at 253° – 255° C for 6 minutes, and then cooled to room temperature. The addition of 20 ml of n-hexane resulted in the precipitation of a solid which was collected, and washed with chloroform. Recrystallization of the solid from dimethylformamide gave the title compound, m.p. 300° C with decomposition.

EXAMPLE 30

Ethyl 7-chloro-1,4-dihydro-1-ethyl-4-oxo-1,6-naphthyridine-3-carboxylate and free carboxylic acid To a solution of 1.28 g of ethyl 7-chloro-1,4-dihydro-4-oxo-1,6-naphthyridine-3-carboxylate in 100 ml of ethanol was added a solution of 1.05 of potassium carbonate in 10 ml of water, and then 2.4 g of ethyl iodide. The resulting mixture was heated to reflux for 1.5 hours and then concentrated to dryness in vacuo. The residue was taken in chloroform and the chloroform solution was washed with water, and dried. Removal of the solvent gave a solid which was recrystallized from ethanol to yield the ester, m.p. 187.5° – 188.5° C.

This ester was hydrolyzed by the usual method to the free carboxylic acid, 7-chloro-1,4-dihydro-1-ethyl-4-oxo-1,6-naphthyridine-3-carboxylic acid, m.p. 260° – 262° C.

EXAMPLE 31

7-Chloro-1,4-dihydro-4-oxo-1-vinylquinoline-3-carboxylic acid.

To a mixture containing 23.4 g of ethyl 7-chloro-1,4-dihydro-4-oxoquinoline-3-carboxylate and 6.9 g of 65% sodium hydride was added 90g of 2-tosyloxyethyl chloride. The resulting mixture was heated at 100° C for 4 hours. After concentration to dryness, the residue was extracted with chloroform. The extract was washed with water, and dried over anhydrous sodium sulfate. The solvent was removed by the distillation to leave a solid which was recrystallized from ethanol to give ethyl 7-chloro-1-(2-chloroethyl)-1,4-dihydro-4-oxoquinoline3-carboxylate, m.p. 207.5°–209.5° C.

To 15 g of the ester obtained above was added 240 ml of a 10% aqueous solution of sodium hydroxide and 100 ml of ethanol. The resulting mixture was refluxed for one hour and filtered with decolorlizing charcoal.

The pH of the filtrate was adjusted to 1 with hydrochloric acid and the solution was chilled to give a precipitate which was collected, washed with water, and recrystallized from dimethylformamide to yield the title compound m.p. 269° – 269° C.

EXAMPLE 32

7-Chloro-1,4-dihydro-4-oxo-1-vinyl-1,8-naphthyridine-3-carboxylic acid

A mixture containing 5.0 g of ethyl 7-chloro-1-(2-chloroethyl)-1,4-dihydro-4-oxo-1,8-naphthyridine-3-carboxylate, 4.3 g of sodium methoxide and 30 ml of methanol was heated to reflux for 1 hour, then concentrated to about 10 ml and water (20 ml) was added. The resulting solution was heated again to 90° C for hours, cooled, and acidified with acetic acid to give a precipitate, which was collected and washed with methanol. The precipitate was added to 20 ml of phosphorus oxychloride and the mixture was heated to 90° C for 45 minutes. After removal of the excess of phosphorus oxychloride by distillation under reduced pressure, the residue was poured into ice-water. The mixture was extracted with chloroform. The extract was washed with water, dried, and concentrated to dryness to give a crude solid, which was recrystallized from ethanol to give 2.9 g of the product, m.p. 235° 14 238° C.

Other compounds of the formula (a) can be prepared in the same way as in Example 29 to 32 by using the corresponding starting material in place of 4-amino-2-chloropyridine in Example 29, using the alkyl ester of ethoxymethylene malonic acid in place of ethyl ester in Example 29, using the alkylating agent, e.g. benzyl bromide, in place of ethyl iodide in Example 30, or using the corresponding starting material in place of the quinoline derivative in Example 31, respectively.

Two of the compounds of the formula (a) are known compounds; i.e., 7-chloro-1,4-dihydro-1-ethyl-4-oxoquinoline-3-carboxylic acid and 7-chloro-1,4-dihydro-1-ethyl-4-oxo-1,8-naphthyridine-3-carboxylic acid.

The preparation for the intermediate compound of the formula (c) is illustrated as follows.

EXAMPLE 33

Diethyl 6-(4-methyl-1-piperazinyl)-2-pyridylaminomethylenemalonate

A mixture containing 2.5 g of 6-amino-2-(4-methyl-1-piperazinyl)pyridine and 3.1 g of diethyl ethoxymethylenemalonate was heated at 90° C for 2 hours and then chilled. The resulting solid was recrystallized from benzene to give the product, m.p. 114°– 115° C.

Other compounds of the formula (c) can be prepared in the same way as in Example 33.

Example 34

| | |
|---|---|
| 1,4-Dihydro-1-ethyl-4-oxo-7-(1-piperazinyl)quinoline-3-carboxylic acid hydrochloride | 250 g |
| Starch | 54 g |
| Calcium carboxymethyl cellulose | 40 g |
| Microcrystalline cellulose | 50 g |
| Magnesium stearate | 6 g |

The above components are blended, granulated and made into tablets in a manner known per se. Thus, 1000 tablets each weighing 400 mg are formed.

Example 35

| | |
|---|---|
| 1,4-Dihydro-1-ethyl-4-oxo-7-(1-(piperazinyl)-1,6-naphthyridine-3-carboxylic acid | 250 g |
| Starch | 50 g |
| Lactose | 35 g |
| Talc | 15 g |

The above components were blended and granulated and filled into 1,000 capsules in accordance with conventional methods.

Example 36

| | |
|---|---|
| 1,4-Dihydro-1-ethyl-4-oxo-7-(1-piperazinyl)-1,8-naphthyridine-3-carboxylic acid | 5 g |
| Sorbitol | 30 g |
| Sugar | 40 g |
| Methylparaben | small amount |
| Sodium carboxymethyl cellulose | small amount |
| Flavour | small amount |
| Water to make | 100 ml |

What is claimed is:

1. A compound of the formula $$R_1-N\underset{}{\overset{}{\bigg\langle}}N-\underset{B}{\overset{A}{=}}\underset{\underset{R_2}{N}}{\bigg|}\overset{O}{\underset{}{\bigvee}}COOR_3$$

wherein:
A and B are carbon or nitrogen, provided that A and B are not both nitrogen;
$R_1$ is hydrogen, alkyl having 1 to 4 carbon atoms, benzyl, or acetyl;
$R_2$ is hydrogen, alkyl having 1 to 4 carbon atoms, benzyl, or vinyl and
$R_3$ is hydrogen or alkyl having 1 to 6 carbon atoms; or the pharmaceutically acceptable acid addition or alkali metal salts thereof.

2. The compound or salt of claim 1 wherein:
$R_1$ is hydrogen, methyl, or ethyl;
$R_2$ is ethyl, or vinyl; and
$R_3$ is hydrogen.

3. The compound or salt of claim 2 wherein A and B are carbon.

4. The compound of claim 2 wherein A is carbon and B is nitrogen.

5. The compound or salt of claim 2 wherein A is nitrogen and B is carbon.

6. The compound or salt of claim 2 wherein $R_2$ is vinyl.

7. The compound or salt of claim 1 wherein:
$R_1$ is hydrogen;
$R_2$ is ethyl; and
$R_3$ is hydrogen.

8. The compound or salt of claim 1 wherein:
$R_1$ is methyl;
$R_2$ is ethyl; and
$R_3$ is hydrogen.

9. The compound or salt of claim 1 wherein $R_2$ is vinyl.

10. The compound or salt of claim 2 wherein A is carbon and $R_2$ is vinyl.

11. The compound or salt of claim 10 wherein B is nitrogen.

12. The compound or salt of claim 10 wherein B is carbon.

13. The compound or salt of claim 11 wherein $R_1$ is hydrogen.

14. The compound or salt of claim 12 wherein $R_1$ is methyl.

15. The compound or salt of claim 12 wherein $R_1$ is ethyl.

16. An antibacterial pharmaceutical composition comprising: an active ingredient consisting essentially or salt of the compound or salt of claim 2 present in a pharmaceutically effective amount; and in admixture therewith at least one pharmaceutically acceptable adjuvant which is inert to the compound.

* * * * *

UNITED STATES PATENT AND TRADEMARK OFFICE
CERTIFICATE OF CORRECTION

PATENT NO. : 4,017,622

DATED : April 12, 1977

INVENTOR(S) : MINAMI, ET AL.

It is certified that error appears in the above-identified patent and that said Letters Patent are hereby corrected as shown below:

Item 30, insert the following:

-- Jan. 30, 1974  JAPAN ................. 49-13172
   June 17, 1974  JAPAN ................. 49-69428 --

Claim 4, line 1, before "of" insert -- or salt --

Claim 16, line 3, delete "or salt" in the first instance.

Signed and Sealed this

Twenty-eighth Day of June 1977

[SEAL]

Attest:

RUTH C. MASON  
Attesting Officer

C. MARSHALL DANN  
Commissioner of Patents and Trademarks